United States Patent [19]

Corbin et al.

[11] 4,044,774
[45] Aug. 30, 1977

[54] PERCUTANEOUSLY INSERTED SPINAL CORD STIMULATION LEAD

[75] Inventors: Terry Corbin, Crystal; Duane J. Zytkovicz, Minneapolis, both of Minn.

[73] Assignee: Medtronic, Inc., Minneapolis, Minn.

[21] Appl. No.: 660,353

[22] Filed: Feb. 23, 1976

[51] Int. Cl.² ............................................. A61N 1/04
[52] U.S. Cl. ............................... 128/404; 128/419 R
[58] Field of Search ................. 128/404, 418, 419 C, 128/419 E, 419 F, 419 P, 419 R

[56] References Cited

U.S. PATENT DOCUMENTS

| | | | |
|---|---|---|---|
| 3,348,548 | 10/1967 | Chardack | 128/418 |
| 3,568,660 | 3/1971 | Crites | 128/419 PX |
| 3,788,329 | 1/1974 | Friedman | 128/418 |
| 3,924,639 | 12/1975 | Hess | 128/418 |

FOREIGN PATENT DOCUMENTS

| | | | |
|---|---|---|---|
| 84,040 | 8/1971 | Germany | 128/419 P |

OTHER PUBLICATIONS

Nathan et al., "Temporary–Permanent...Surgery", J. of Thorac & C. Surgery, vol. 64, 1972, pp. 957–958.
"Temporary Pacing Postoperatively in many Cardiac Surgery Patients", Cordis Corp., 1975.

Primary Examiner—Robert W. Michell
Assistant Examiner—Lee S. Cohen
Attorney, Agent, or Firm—Cameron, Kerkam, Sutton, Stowell & Stowell

[57] ABSTRACT

A lead is disclosed for being inserted within a human or animal body for applying electrical stimulation to the spinal cord of the recipient, whereby selected pain is effectively relieved by the application of an electrical signal of selected frequency, pulsewidth and amplitude to the lead. In particular, the lead comprises a spherically-shaped, distal electrode adapted to be disposed near a selected segment of the spinal cord whereby maximum stimulation may be applied to the afferent nerves passing therethrough, a first conductor taking the form of a helically-wound coil extending from the distal electrode to a first tubular contact, and a second conductor disposed axially of the first-mentioned coil and forming an extension extending beyond the first-mentioned contact and terminated in a second tubular contact.

21 Claims, 3 Drawing Figures

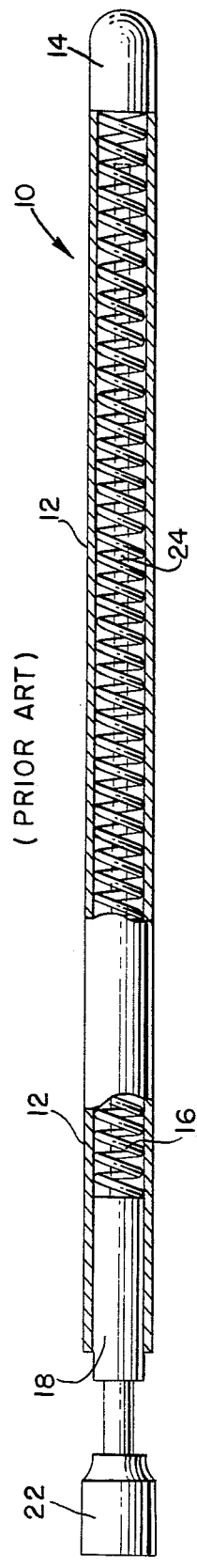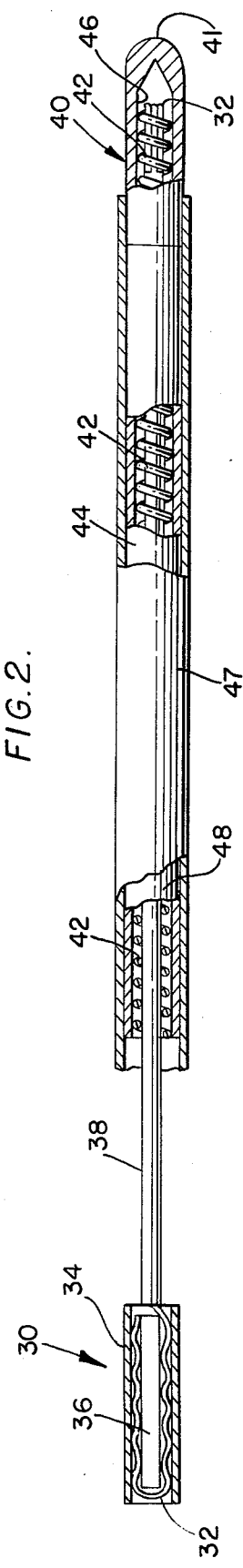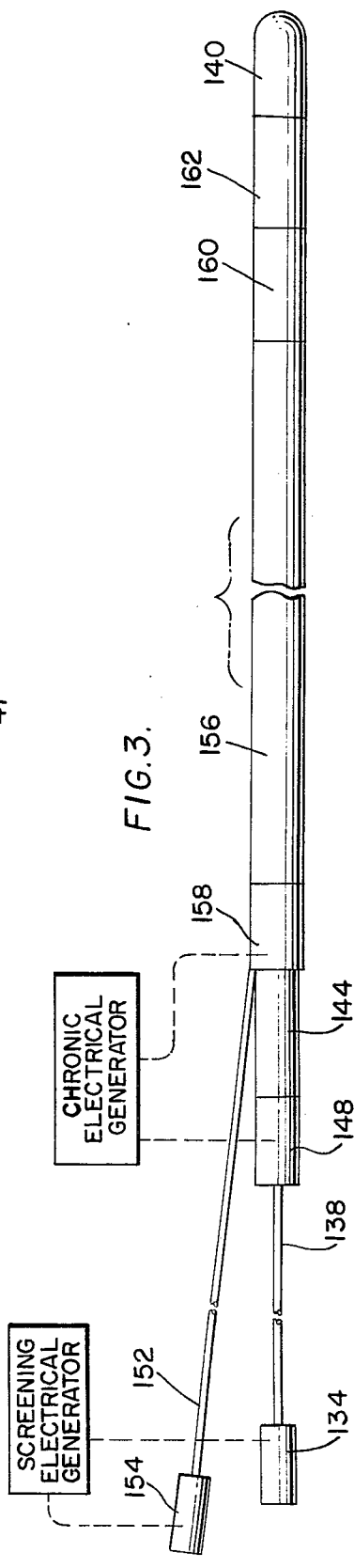

PERCUTANEOUSLY INSERTED SPINAL CORD STIMULATION LEAD

BACKGROUND OF THE INVENTION

1. Field of the Invention

This invention relates to medical apparatus and more particularly to an implantable lead for electrical stimulation of selected portions of the body of the animal in which the lead is implanted and in particular the spinal cord thereof. The word "animal" is here used in its broad sense, including Homo Sapiens.

2. State of the Prior Art

It has long been known to transmit and apply electrical signals to and from the body by way of electrical contact, either with the skin or with respect to a particular organ therein. For example, electrical stimulation has been applied to the heart to stimulate the heart into contracting and expanding at a prescribed, selected rate, as described in U.S. Pat. No. 3,057,356 of W. Greatbatch and assigned to the assignee of the subject invention. In addition, it has been known to apply an electrical signal to the skin to accomplish an electrical "treatment" as discussed in U.S. Pat. Nos. 1,059,090 and 1,305,725. As medical science has advanced, it has been increasingly realized that electrical signals may be applied to relieve or at least block the sensation of pain and in partiular chronic intractable pain. Chronic, intractable pain, by definition implies that all conservative medical treatments aimed at the pain-causing lesion have been instituted and performed respectively. When such procedures fail, the physician and in particular the neurosurgeon, is faced with the finality of destroying a portion of the nervous system tissue in an attempt to sever the pathways of the pain stimulus to the brain, or, in severe cases, to remove portions of the brain tissue itself. For decades, research has been directed at developing more desirable neurosurgical approaches to consistent ablation of chronic, intractable pain. To this end, it has been discovered that electrical stimulation may be selectively applied to the dorsal column or spinal column of the patient, whereby controlled interruption of pain transmission provides a non-destructive approach to the management of pain and care for selected patients.

It has been demonstrated physiologically that all pain information travels through the spinal cord via gamma-delta or C-fibers. Also, stimulaion of the larger A-beta fibers is never painful. It has been hypothesized that activity in beta-fibers inhibits, at the first spinal synapse, immediate subsequent activity from the smallest fibers considered essential to pain conduction. As discussed in the publication, "Pain Mechanisms: A New Theory", by Melzack and Wall, SCIENCE, 1965, Vol. 150, pp. 971-973, this mechanism may act to balance pain and non-pain input. It has been experimentally demonstrated, as reported by C. N. Shealy et al in "Electrical Inhibition of Pain: Experimental Evaluation", Anesth. Analg. Curr. Res., 1967, 46:299, that the pain threshold may be increased by 12,-fold during dorsal column stimulation. This technique has subsequently been applied to human patients with chronic intractable pain. In response thereto, patients sense paresthesiae, i.e. a buzzing or tingling sensation, that radiates downward through much of the body below the implanted electrode.

To relieve pain through dorsal column stimulation, the electrode is implanted and connected by a lead to a receiver which also may be implanted within the patient's body. Typically, a transmitter is provided externally of the patient for exciting the implanted transmitter, whereby an electrical signal of selected frequency, amplitude and duration, is applied to the electrode inserted within the dorsal cord. Clinical results indicate that efficient pain relief occurs only in those areas where the paresthesiae is sensed. Thus, as will be discussed in some detail later, it is significant to have patient response as to the paresthesiae and his pain relief in order to ensure the maximum efficient use of dorsal column stimulation. It has been shown that the use of electrical stimulation has many advantages over the use of drugs or destructive surgery wherein a portion of the peripheral or central nervous system tissue is destroyed, to relieve intractable pain. Drugs invariably have the disadvantage of undesirable physiological side effects as well as mental obtundation or addition, or both. Destructive surgery (primarily cordotomy or rhizotomy) carries substantial risk of weakness, numbness, dysesthesia, bladder or bowel incontinence, impotentia and irreversibility.

Typically, such dorsal column stimulator systems contain a radio frequency transmitter, a transmitting antenna, both of which are positioned externally of the patient's body, and an RF receiver and a stimulating lead implanted, as will be explained, within the patient's body. The transmitter supplies stimulating power of a selected frequency, amplitude and pulsewidth to the receiver by inductive coupling through the patient's skin. In operation, the antenna is placed on the skin directly over the implanted receiver, whereby an inductive coupling is established therebetween. The receiver shapes the RF signals into appropriate waveform and applies this electrical energy via the implanted leads to the dorsal column.

In the prior art, the leads have been implanted, typically by a procedure known as a "bilateral laminectomy" wherein a skin incision is made of sufficient length to expose the dura mater to implant a pair of electrodes to stimulate the afferent nerve disposed within the spinal cord, whereby the transmission of pain therethrough is essentially blocked. A laminectomy is considered to be major surgery in that two or three spinous processes and one set of lamina are removed, with resultant trauma upon the patient. In addition, a transverse incision is made, centered over the clavical, for the placement of the receiver, and a subcutaneous tunnel is developed from this incision over the shoulder to the laminectomy site.

In any surgical procedure for the implantation of pain-relieving leads, whether by a laminectomy or by another procedure to be described, it is desirable to have a percutaneous screening or testing period, wherein the physician and/or the patient may test the reaction of the patient to the stimulator to block pain. During this screening period, the patient may well have an adverse reaction in terms of pain or discomfort due to the implantation or, for some reason, the electrical stimulation may not have the desired effect. In carrying out the above-discussed laminectomy, it is desirable because of the major nature of the surgery carried out, that the patient be completely anesthetized. As a result, it is not possible for the physician to use a local anesthetic, whereby the patient's reaction to the stimulation may be tested. Otherwise, it would be possible if the patient could be mildly anesthetized in the region of the implantation, to adjust the position of the electrodes with respect to the afferent nerves, to ensure maximum pain relief sensation at mimimum levels of excitation in terms of amplitude and/or pulsewidth, noting that as these parameters increase, battery life and possible adverse effects are respectively reduced and increased. Before a typical laminectomy procedure, the neurosurgeon places a pair of temporary leads within the spinal canal by a percutaneous procedure. If the electrodes of these leads are accurately placed and the patient is appropriately responsive to the electrical stimulation, the electrode site within the patient may be exposed by laminectomy and the temporary leads replaced with permanent leads; the difficulty with such a replacement is that the electrode position may well be changed with the result that the subsequent positioning of the electrodes of the permanent leads with respect to the afferent nerves is not as beneficial.

The significance of the percutaneous screening resides in the opportunity to obtain the patient's reaction to such electrical stimulation and to the implantation of a foreign body within his body. For example, the patient may not be psychologically conditioned to receive such an implant in that he may be dependent upon such pain to obtain attention from friends and relatives or may be monetarily dependent thereon to receive financial aid. In addition, the potential success of such electrical stimulation to reduce pain may be lessened by the previous history of using medication, including narcotic drugs, for pain alleviation. In either case, a patient may not be a suitable candidate for implantation and it would be desirable to test his reaction to such stimulation during a testing or screening period.

Due to the possible adverse effects of a laminectomy, other less strenuous surgical procedures have been developed wherein the patient may be subjected to a local anesthesia in the vicinity of the electrode implantation site and the receiver site. Typically, as described in a manuscript entitled, "Percutaneous System for Epidural Stimulation", as published by the Avery Laboratories, Inc. of Farmingdale, N.Y., the patient is prepared in a prone position with local anesthesia, and a hypodermic needle having a first electrode lead disposed therein is inserted under radiographic control between two vertebrae, several spaces below the desired level of stimulation. The opening of the needle tip should be directed cephald and should ultimately be within the epidural space. Next, a second electrode lead is inserted by a second hypodermic needle, one space below the first, under radiographic control so that the opening of the needle is within the epidural space and facing cephalad on the midline of the spinal cord. At this point, the tips of the two inserted electrodes are disposed within the epidural space and should lie from 1 to 5 cm above or below each other, as close to the midline as possible. Next, an incision is made through the subcutaneous tissue between the two needle punctures that serves as a site for the electrode plant, and then each hypodermic needle is withdrawn over the electrode lead wire. A further incision to form a connector pocket is made approximately 4 cm lateral to the first incision, and a tunnel is made therebetween through which the first and second leads associated with the aforementioned electrode tips, are passed. At this point, the remote contacts of the leads are temporarily connected to a stimulating generator and suitable stimulation is applied to the leads, whereby the placement of the electrodes within the spinal cord may be slightly adjusted to achieve maximum stimulation. The incisions are closed, with the temporary leads passing externally through the skin to be connected to the test stimulating generator. If the percutaneous screening proves successful, it is then desired to implant the receiver within the receiver pocket. To this end, the connector pocket is opened so as to not damage the electrode leads or the temporary connectors, and these are subsequently disengaged. Next, the temporary connectors are withdrawn and the receiver pocket is formed to receive the receiver and a new tunnel is formed between the receiver site and the connector pocket. Subsequently, the receiver is inserted and its leads are passed through the new tunnel to the connector pocket and subsequently interconnected with the electrode leads. At this time, all the incisions are closed. Thus, if it were desired to conduct percutaneous screening, it is necessary in utilizing such a procedure to form three incisions within the patient. Further, there is the possibility in disconnecting the temporary leads from the electrode leads that it would be necessary to withdraw the ends of both to effect the disconnection; in carrying out this step, it is a distinct possibility that the electrode placement near the dorsal cord may be disturbed, thus negating the original accurate placement by the neurosurgeon. In addition, it is necessary to make an extra incision within the patient before it is decided whether he is adaptive to receive such chronic implantation.

Reference is now made to FIG. 1, marked "Prior Art", which shows an electrode assembly as may be well used in a procedure as described above. Though only a single lead is shown in FIG. 1, it is understood that two such leads would be inserted. In FIG. 1, there is shown a lead 10 comprising at its distal end, an electrode 14 made of a suitable electrically conductive metal capable of being implanted within the body without corrosion, such as platinum. A flexible conductor 16 extends from the electrode 14 to a rigid, typically metallic male connector pin 18. Further, a sheath 12 of a suitable insulating material adapted to be implanted within the human body, is disposed about the conductor 16, which may illustratively be a helically-wound wire, such as a platinum-iridium alloy. The helically-wound conductor 16 is connected at its proximal end to the pin 18 and extends along the length of the lead 10 to be connected to the electrode 14. In addition, a stainless steel stylet 22 may be disposed within a lumen or hollow passage 24 of the connector pin 18 and conductor 16, to assist the surgeon in guiding the lead 10 into its correct position. As generally illustrated in FIG. 1, the stylet 22 extends through an opening within the pin 18 into the lumen 24, and into and along substantially the entire length of the lead 10.

As described above, the surgical procedure for inserting such a lead 10 requires that a second, temporary lead be connected thereto, to be withdrawn through a third incision within the patient before the test period is begun. In addition, such a lead does not facilitate the ready interconnection to the receiver to be implanted with the result that the placement of its electrode 14 may be slightly disturbed during the permanent implantation of the receiver, so that a less than maximum stimulation of the patient is subsequently achieved.

SUMMARY OF THE INVENTION

Therefore, it is an object of this invention to provide an implantable lead particularly adapted for accurate placement within the human body and in particular with respect to that portion of the nervous system to be stimulated.

It is a further object of this invention to provide an implantable lead that facilitates a temporary connection to a test or temporary source of electrical stimulation and a subsequent permanent connection to a second source of electrical stimulation.

In accordance with these and other objects of the invention, there is provided a lead having an electrode disposed at its distal end and a first conductor electrically connected thereto and extending a first distance to a first contact, the first conductor being surrounded and electrically insulated by a suitable insulating material, and a second conductor extending from the electrode along the lead a second distance to a second contact, the second distance being selected such that the extended portion permits the second contact to be withdrawn outside of the patient's body to permit a temporary electrical connection between the second contact and a temporary or test source or generator of electrical stimulation. In order to facilitate the reconnection of the lead to a permanent source of electrical stimulation, the second conductor and its electrically-insulating material disposed thereabout are readily severable to permit the extended portion to be readily removed at the time of reconnection. In this regard, the first contact is adapted to be connected easily to the permanent source of electrical stimulation.

In a further feature of this invention, the first conductor is formed in a coil about the second conductor, whereby the combination of the first and second conductors forms a relatively flexible electrode that is capable of being inserted by a needle into its desired position and permitting ready withdrawal of the needle while retaining the electrode lead implanted within the patient's body.

BRIEF DESCRIPTION OF THE DRAWINGS

These and other objects and advantages of the present invention will become more apparent by referring to the following detailed description and accompanying drawings, in which:

FIG. 1 shows a partially broken-away view of a lead of the prior art;

FIG. 2 shows a partially sectioned view of a lead in accordance with the teachings of this invention, including an extended portion adapted to be connected to a temporary or test source of electrical stimulation; and FIG. 3 shows an alternative embodiment of this invention including a first distal electrode and a second, proximal electrode and corresponding temporary extensions connected thereto.

DETAILED DESCRIPTION OF THE PREFERRED EMBODIMENTS

Referring to the drawings and in particular to FIG. 2, there is shown an illustrative embodiment of this invention as comprising a lead 30 comprising an electrode 40 disposed at the leading end of the lead 30 having a rounded end 41 to permit facile insertion through an inserting needle and into the patient's body, and made of a suitable electrically conductive material capable of being disposed within the environment of the human body without corrosion, such as platinum. The electrode 40 is in one illustrative embodiment of this invention, 0.160 inches in length and has an opening 46 therein of a depth of 0.125 inches for receiving a first conductor 42 in the form of a coil and a second conductor 32. As more clearly shown in FIG. 2, the coiled, first conductor 42 extends from the electrode 40, a first distance illustratively in the order of 11 inches to a first contact 48. As illustrated, the first conductor 42 takes the form of a coil of a wire illustratively made of a nickel alloy and having a diameter of approximately 0.06 inches and wound into a coil having an outer diameter of 0.024 inches. The first contact 48 illustratively takes the form of a tubular-shaped member, illustratively made of platinum and disposed over the coiled, first conductor 42 and held thereto by crimping. The first contact 48 is ordinarily electrically insulated by a thin coating of silicone rubber to prevent inadvertent stimulation of tissue prior to its permanent connection to a receiver. The second conductor 32 extends from the electrode 40 past the first contact 48 to a second contact 34 similar to the first-described and in one illustrative embodiment of this invention, has a length in the order of approximately 42 inches. As will be explained in detail later, the second conductor 32 forms an extension that is used during the percutaneous screening or testing period. Thus, while the portion of the lead 30 extending from the electrode 40 to the first contact 48 is implanted within the patient's body, the remaining portion of the lead 30 including the second contact 34 is withdrawn from the patient's body to be connected to a test source or generator of electrical stimulation. At the end of the percutaneous screening period, the second conductor 32 is removed as by severing same adjacent to the first contact 48. In an illustrative embodiment of this invention, the second conductor 32 takes the form of a 15-strand stainless steel wire that is covered by an insulating layer 38, e.g. Teflon, and having an illustrative diameter of 0.009 inches. As shown in a broken-away section of FIG. 2, the stranded, second conductor 32 is stripped of its insulating layer 38 and is disposed about a length of a wire 36, illustratively a stainless steel wire of a diameter of approximately 0.020 inches and a length of approximmately 0.15 inches. The second contact 34 taking the form of a tubular-shaped, electrically conductive member made illustratively of stainless steel, is disposed about the conductor 32 and the wire 36, and crimped thereon.

In fabrication, the second conductor 32, including its insulating layer 38 is disposed within the coil-shaped first conductor 42, as seen in the broken-away portion of the electrode 40, the insulating layer 38 is stripped away and the strands of the wire 32 are directed back over the coiled, first conductor 42. At this point, the assembled first and second conductors 42 and 32 are inserted within the opening 46 of the electrode 40 and is swaged to mechanically and electrically connect the electrode 40 to both of the first and second conductors 42 and 32. Next, an insulating sheath 44 made of a suitable insulating material adapted to be disposed within the environment of the human body, such as a silicone rubber or polyurethane, is disposed within a suitable solvent such as acetone whereby the sheathing 44 is slightly expanded, before it is slipped over the coiled, first conductor 42; as the solvent evaporates, the insulating sheath 44 contracts about and is securely held to the coiled, second conductor 32. As shown in FIG. 2, a first edge of the sheath 44 abuts intimately the trailing edge of the electrode 40. The insulating sheath 44 extends only part-way along the length of the first conductor, thus permitting the first contact 48 to be disposed about the remaining portion of the coil 42 and crimped thereto as explained above. Finally, the second tubular contact 34 is assembled and in particular is crimped about the second conductor 32 and the wire 36 in a manner as explained above. The first tubular contact 48 is coated with silicone rubber for insulation during screening.

The advantages of the use of the lead 30 as shown in FIG. 2 will become more apparent as the surgical procedure for its implantation to permit percutaneous screening and the subsequent chronic implantation are now described. First, the patient is prepared for surgery, using a light preoperative medication in the form of a local anesthetic, so that the patient will be available to inform the doctor as to the optimum placement of the first and second leads as shown in FIG. 2. For pain applications, the traditional placement of the electrodes of the leads is a few segments above the point where the afferent nerves from the painful area enter the spinal cord. Typically, the electrodes 40 are placed one above the other along the midline of the spinal cord, with a spacing of approximately 1 cm therebetween. Alternatively, the electrodes 40 may be placed a few mm laterally of each other, toward the side of greatest pain. The first of the leads 30 is inserted within a Tuohy needle, characterized by its curved, pointed end and partially shown in FIG. 2 as element 47. The Tuohy needle is inserted between the spinous processes for the first, superior lead. To determine when the tip of the needle is in the epidural space adjacent the spinal cord, the obturator of the needle is removed and a drop of sterile saline solution is placed in the hub of the needle. If its tip is correctly placed, the saline solution will be drawn through the needle into the epidural space, indicating that a correct location has been achieved. An optional step is the introduction of approximately 5 cc of filtered air to inflate the epidural space. Now, the lead 30 is introduced and advanced several segments cephalad (toward the patient's head) from the tip of the inserted needle. At this point, the second contact 34 is connected directly to the negative terminal of the pulse generator such as a Model 3620 or Model 3721 stimulator, as manufactured by the assignee of this invention. In a similar fashion, the second lead 30 is inserted by a second Tuohy needle within the patient, one space along the patient's spinal cord below the first needle. In turn, the second lead 30 is connected to the positive terminal of the pulse generator, and the thus-inserted pair of leads 30 is electrically stimulated while the second lead 30 is advanced to achieve the optimum position of the two electrodes 40 thus inserted. This is achieved by receiving the comments of the patient as to his sensation of his paresthesiae in the area of pain, while the attending physician adjusts the level of stimulation to achieve the maximum pain relief for the lowest-possible stimulation level.

With the needles still in place, an incision is made between the needles and extending past each one approximately 2 cm. This incision should extend in depth to the lumbo-dorsal fascia and thereafter, the needles are carefully removed, with care taken not to dislodge the electrodes 40. In this regard, the Tuohy needle has a relatively larger diameter in the order of 0.055 inches, greater than the outer diameter of the lead 30 to permit its ready withdrawal. Thereafter, the second contacts 34 are reconnected to the source of stimulation for a check of electrode position. If the electrodes 40 have been moved, the leads 30 should be advanced or withdrawn until an acceptable result is attained.

At this time, one of the Tuohy needles is threaded to an anchoring patch of artificial dura several times, and thereafter, the patch is advanced down the lead wires to the tissue and sutured to the fascia at each corner. Thereafter, stimulation again is applied to recheck the electrode position. Then a tunnel is created for that portion of the lead 30 extending from its electrode 40 to its first contact 48; this is done by choosing a point, illustratively 7 inches lateral to the first-made incision at the electrode site. At this point, a needle puncture is made through the skin to provide a lead exit site. Thereafter, the leads 30 are directed through a somewhat larger needle to the chosen lead exit site and thereafter the larger needle may be removed and the leads pulled so that no slack of the lead lies in the tunnel or the incision. The small diameter and absence of oversized connectors of the leads 30 allows the surgeon to create a small tunnel under local anesthesia, lessening trauma and cosmetic damage to the patient's skin.

Again, stimulation is applied through the second contact 34 and the second conductor 32 and continued during the closure of the incision. At this point, a substantial portion of the extension of each of the two leads 30 passes through the patient's skin and is available to be connected to the source of stimulation during the percutaneous evaluation or screening phase, which typically requires 3 to 5 days. During this period, the patient and his physician evaluate the degree of pain relief, as well as any side effects in terms of possible pain due to the implantation. The significant advantage of the use of the lead 30 as shown in FIG. 2 is that it is not necessary to make either a second or third incision in the patient's body or a tunnel between the second and third incisions for the placement of an additional temporary lead to be used during the percutaneous evaluation phase; rather, only one incision is made in preparation for the testing phase, and the extension of the lead 30 is brought directly through the skin, thus minimizing the surgery performed upon the patient and the possibility of electrode displacement.

If the results of the percutaneous testing phase are satisfactory to both the physician and the patient, the system then is converted for chronic, radio frequency coupled stimulation employing an external battery-powered stimulation transmitter, such as the Medtronic Model 3521, connected to an external antenna, such as the Medtronic Model 4040, and an implanted receiver, such as the Medtronic Model 3570 which is in turn connected to the leads 30. In particular, the patient is positioned in the lateral decubitus position so that the lead wire exit point is accessible, and subsequently a general or local anesthesia is applied. First, a conductor incision is made at the site where the extended portion of the lead 30 joins the larger-diameter portion of the lead at the first contact 48. At this point, the second conductor 32 and insulating layer 38 are severed as by a pair of scissors, at a point as close to the first contact 48 as possible, and then simply discarded. Thereafter, a pocket is made to receive the receiver within the patient's abdomen, lateral thigh, or below the clavicle, depending on the electrode positions. A tunnel then is formed between the incision exposing the second contact 48 to the receiver pocket site, by blunt dissection. It is also understood that the receiver or generator, as illustratively shown in FIG. 3, has an extension conductor, such as the Medtronic Model 3490, connected thereto having at its remote end a socket-type connector adapted to be disposed about and connected to the second contact 48, as by a small set-screw. The receiver extension is pulled through the tunnel to the conductor incision and the socket connectors thereof are disposed about the second contacts 48 and their set-screws are tightened. The set-screws cut through the silicone rubber coating of the contacts 48 to make efficient electrical and mechanical connection. Thereafter, a small silicone rubber boot is advanced up each of the receiver leads and is disposed over the socket connector and filled with a medical adhesive. The boot then is secured at both ends with non-absorbable sutures. Thereafter, the conductor incision and the receiver incision both are closed. Note that the procedures for removing the extension and the second connector and for connecting the receiver extension to the second contact 48 are relatively simple, thereby assuring that the original placement of the electrodes 40 of both of the leads 30 is not disturbed, thereby ensuring that the maximum degree of pain relief is not disturbed during the implantation of the receiver.

In FIG. 3, there is shown a further embodiment of this invention in the form of a bipolar embodiment comprising a first or distal electrode 140 and a second or proximal electrode 160, that are adapted to be disposed within the patient's body for pain relief stimulation. Whereas the first embodiment as shown in FIG. 2 is particularly designed for spinal cord stimulation, the bipolar embodiment of FIG. 3 may be adapted for other tissue stimulation, e.g. brain stimulation for alleviation of chronic pain or spasticity due to cerebral palsy or epilepsy. As indicated in FIG. 3, the distal electrode 140 is connected to first and second distal contacts 134 and 148, respectively, by a first conductor (not shown) passing through an insulating sheath 138. In a similar fashion, the proximal electrode 160 is connected to the first proximal contact 158 by a second conductor taking the form of a helical winding and passing through an insulating layer 156 to the second proximal contact by a third conductor covered by an external insulating sheathing 152. As shown in FIG. 3, the proximal and distal electrodes 160 and 140 are separated from each other by an insulating sheathing 162, and also the contacts 148 and 158 are separated from each other by a insulated sheathing 144. The manner of interconnecting the various conductors to the electrodes 160 and 140, as well as to the contacts 134, 148, 154 and 158, as well as the choice of materials of which to make the bipolar electrode may illustratively be similar to those as described above with respect to FIG. 2.

Numerous changes may be made in the above-described apparatus and the different embodiments of the invention may be made without departing from the spirit thereof; therefore, it is intended that all matter contained in the foregoing description and in the accompanying drawings shall be interpreted as illustrative and not in a limiting sense.

What is claimed is:

1. A lead adapted to be attached to and extended between first and second sources of electrical stimulation and animal tissue to conduct and apply such stimulation to the tissue, comprising:
   a. a stimulation electrode of an electrically conductive material substantially inert to body fluids and tissues;
   b. a first conductor having a distal end electrically connected to said stimulation electrode and extending therefrom a first distance along said lead to a proximal end thereof;
   c. a first electrical contact electrically connected to said proximal end of said first conductor, and adapted to be connected to the first source of stimulation to be applied along said first conductor to said stimulation electrode for stimulating the animal tissue;
   d. a second conductor having a distal end electrically connected to said stimulation electrode and extending a second distance along said lead to a proximal end of said second conductor, said second distance being greater than said first distance;
   e. a second electrical contact electrically connected to said proximal end of said second conductor and adapted to be connected to the second source of stimulation whereby electrical stimulation may be applied through said second conductor to said stimulation electrode; and
   f. a sheath of an electrically insulating material substantially inert to body fluids and tissues and covering said first and second conductors between said stimulation electrode and said first and second contacts, said second conductor and said sheath covering said second conductor between said first and second contacts being of a reduced dimension, whereby said second conductor may be readily severed and removed from said lead.

2. The lead as claimed in claim 1, wherein said first conductor is formed as a coil disposed within said sheath.

3. The lead as claimed in claim 1, wherein said first contact is of a tubular configuration and is disposed about said first conductor and crimped thereto.

4. The lead as claimed in claim 1, wherein said first contact is normally covered with an insulating material readily penetrable to facilitate electrical connection of said first contact to the first source of stimulation.

5. The lead as claimed in claim 1, wherein there is included a second stimulation electrode spaced remotely from and insulated from said first stimulation electrode, a third conductor having a distal end connected to said second stimulation electrode and disposed along the length of said lead a third distance less than said first distance to a proximal end, a third contact of an electrically conductive material substantially inert to said body fluids and tissues and connected to said proximal end of said third conductor, a fourth conductor having a distal end electrically connected to said second electrode and disposed along the length of said lead to a proximal end a fourth distance greater than said third distance, and a fourth contact of an electrically conductive material substantially inert to body fluids and tissues and electrically connected to said proximal end of said fourth conductor whereby electrical stimulation may be applied through said fourth conductor to said second stimulation electrode.

6. Medical apparatus implantable in the body of an animal, comprising:
   a. a stimulation electrode of an electrically conductive material substantially inert to body fluids and tissues;
   b. a first conductor having a first, distal end electrically connected to said stimulation electrode and extending therefrom a first distance along said medical apparatus to a second proximal end thereof;
   c. a first electrical contact electrically connected to said second, proximal end of said first conductor, and adapted to be connected to apply stimulation along said first conductor to said electrode for stimulating nerve tissue of the animal;

d. a second conductor having a first, distal end electrically connected to said electrode and extending a second distance greater than said first distance and having a second, proximal end;

e. a second electrical contact electrically connected to said second, proximal end of said second conductor and adapted to be connected to apply stimulation through said second conductor to said stimulation electrode; and f. a first sheath of an electrically insulating material substantially inert to body fluids and tissues and covering said first and second conductors between said stimulation electrode, and said first contact, and a second sheath of an electrically insulating material substantially inert to body fluids and tissues and at least covering said second conductor between said first contact and said second contact, said second conductor and second sheath being of a reduced dimension, whereby it may be readily severed and removed from said medical apparatus.

7. Medical apparatus as claimed in claim 6, wherein said first conductor is formed as a coil disposed about said second sheath, said second sheath extending along substantially the entire length of said second conductor.

8. Medical apparatus as claimed in claim 6, wherein said first contact is of a tubular configuration and is disposed about said first conductor and crimped thereto.

9. The medical apparatus as claimed in claim 6, wherein said first contact is normally covered with an insulating material readily penetrable to facilitate electrical connection of said first contact to the electrical stimulation.

10. Medical apparatus as claimed in claim 6, wherein there is included a second stimulation electrode spaced remotely from and insulated from said first stimulation electrode, a third conductor having a distal end connected to said second stimulation electrode and disposed along the length of said medical apparatus a third distance less than said first distance to a proximal end, a third contact of an electrically conductive material substantially inert to said body fluids and tissues and connected to said proximal end of said third conductor, a fourth conductor having a distal end electrically connected to said second electrode and disposed along said medical apparatus a fourth distance greater than said third distance to a proximal end, and a fourth contact of an electrically conductive material substantially inert to body fluids and tissues and electrically connected to said proximal end of said fourth conductor whereby electrical stimulation may be applied through said fourth conductor to said second stimulation electrode.

11. Apparatus for electrically stimulating animal tissue of the type including a generator for producing chronic electrical stimulation and a lead connected to said generator and comprising a first, permanent conductor having a proximal end including first contact means and a distal end including a stimulation electrode, said first contact means connected to said generator to conduct via said first conductor the chronic electrical stimulation therethrough to its distal end connected to said stimulation electrode, whereby selected, remote animal tissue is stimulated, said lead being constructed of materials substantially inert to body fluids and tissues and further comprising:

a. means for percutaneously admitting said lead into the body and for advancing said electrode into contact with the selected animal tissue;

b. second contact means electrically connected to said electrode of said lead adapted to be connected to a screening generator on advancement of said electrode into contact with the selected animal tissue for eliciting a tissue response to the electrical stimulation impulses; and c. a severable extension conductor extending between said stimulation electrode and said second contact means effecting the electrical connection therebetween and facilitating the application of screening stimulation to the selected animal tissue, said severable extension conductor having a length greater than that of said first permanent conductor.

12. The apparatus as claimed in claim 11, wherein said percutaneous admitting means comprises a tubular needle into which said lead extends.

13. The apparatus as claimed in claim 11, wherein said permanent conductor is formed as a coil disposed within an insulating sheath extending between said stimulation electrode and said first contact means.

14. The apparatus as claimed in claim 11, wherein said first contact means is of a tubular configuration and is disposed about said permanent conductor and crimped thereto.

15. The apparatus as claimed in claim 11, wherein said first contact means is normally covered with an insulating material readily penetrable to facilitate electrical connection of said first contact means to the source of chronic stimulation.

16. Apparatus for electrically stimulating selected segments of a spinal cord, and including a lead having distal and proximal ends and applying electrical stimulation to the selected segments, and operative in a first, screening mode, wherein said lead is connected to a screening electrical generator for applying screening stimulation to said electrode, and in a second mode wherein said lead is connected to a chronic electrical generator for applying chronic electrical stimulation to said electrode, said lead comprising:

a. a stimulating electrode connected to said distal end of said lead for applying electrical stimulation to the selected segments;

b. first contact means disposed at said proximal end of said lead and connected to the chronic electrical generator;

c. a first permanent conductor extending between said electrode and said first contact means for effecting the electrical connection therebetween and facilitating the chronic stimulation of the selected segments;

d. second contact means adapted to be connected to the screening electrical generator; and e. a severable extension conductor extending between said electrode and said second contact means for effecting the electrical connection therebetween and facilitating the screening stimulation of the selected segments, said severable extension conductor having a length greater than that of said first permanent conductor.

17. The apparatus as claimed in claim 16, wherein said permanent conductor is formed as a coil disposed within an insulating sheath of a material substantially inert to body fluid and tissues, said sheath covering said permanent and severable conductors between said electrode and said first contact means.

18. The apparatus as claimed in claim 16, wherein said first contact means is of a tubular configuration and is disposed about said permanent conductor and crimped thereto.

19. The apparatus as claimed in claim 16, wherein said first contact means is normally covered with an insulating material readily penetrable to facilitate electrical connection of said first contact means to the source of chronic stimulation.

20. A lead adapted to apply electrical stimulation to selected animal tissue, comprising:
    a. a stimulation electrode of an electrically conductive material substantially inert to body fluids and tissues;
    b. a first conductor having a distal end electrically connected to said stimulation electrode and extending therefrom a first distance along said lead to a proximal end thereof;
    c. a first electrical contact electrically connected to said proximal end of said first conductor, and adapted to be connected to the first source of stimulation to be applied along said first conductor to said stimulation electrode for stimulating the selected animal tissue;
    d. a second conductor having a distal end electrically connected to said stimulation electrode and extending a second distance along said lead to a proximal end of said second conductor, said second distance being greater than said first distance;
    e. a second electrical contact electrically connected to said proximal end of said second conductor and adapted to be connected to the second source of stimulation whereby electrical stimulation may be applied through said second conductor to said stimulation electrode;
    f. a first sheath of an electrically insulating material substantially inert to body fluids and tissues and covering said first conductor between said stimulation electrode and said first contact;
    g. a second stimulation electrode spaced remotely from and insulated from said first stimulation electrode;
    h. a third conductor having a distal end connected to said second stimulation electrode and disposed along the length of said lead a third distance less than said first distance to a proximal end;
    i. a third contact of an electrically conductive material substantially inert to said body fluids and tissues and connected to said proximal end of said third conductor;
    j. a fourth conductor having a distal end electrically connected to said second electrode and disposed along the length of said lead a fourth distance greater than said third distance to a proximal end;
    k. a fourth contact of an electrically conductive material substantially inert to body fluids and tissues and electrically connected to said proximal end of said fourth conductor whereby electrical stimulation may be applied through said fourth conductor to said second stimulation electrode; and
    l. second and third sheaths of an electrically insulating material substantially inert to body fluids and tissues and covering, respectively, said second and fourth conductors.

21. The lead as claimed in claim 20, wherein each of said second and fourth conductors and said second and third sheaths are of a reduced dimension, whereby said second and fourth conductors may be readily severed and removed from said lead.

* * * * *